United States Patent [19]

Hogan et al.

[11] Patent Number: 4,856,318

[45] Date of Patent: Aug. 15, 1989

[54] SURFACE RESILIENCY TESTER

[75] Inventors: Paul J. Hogan, Phoenixville, Pa.;
Evan Sanders, Tewksbury, Mass.;
Robert DiGirolamo, Springfield, Pa.

[73] Assignee: Playground Clearing House, Inc., Phoenixville, Pa.

[21] Appl. No.: 75,519

[22] Filed: Jul. 20, 1987

[51] Int. Cl.⁴ ............................................. G01N 3/30
[52] U.S. Cl. ........................................ 73/12; 73/82; 73/492
[58] Field of Search ............... 73/12, 492, 82, 573, 73/594, 488, 489, 493

[56] References Cited

U.S. PATENT DOCUMENTS 2,639,210  5/1953  Robertson et al. ............... 73/489 X Primary Examiner—Jerry W. Myracle
Attorney, Agent, or Firm—Eugene E. Renz, Jr.

[57] ABSTRACT

A method and apparatus for determining the suitability of playground, recreation and sports facilities surfaces as well as determining natural or synthetic surface compactness and hardness. The apparatus includes a transducer module consisting of an impact head and a transducer capable of converting impact forces or g's to electrical signals and an electronic module which detects the electrical signal from the transducer, amplifies the peak value and converts it to a digital, numerical reading. The apparatus is adapted to accept a variety of impact heads, transducers and electronic peripherals depending on specific applications.

18 Claims, 4 Drawing Sheets

SURFACE RESILIENCY TESTER

FIELD OF THE INVENTION

The present invention relates to a new and novel apparatus and method for obtaining on-site measurements of resiliency, compactness, and hardness of natural and synthetic surfaces.

More specifically, the invention is a novel, hand-carriable, surface resiliency tester comprised of a transducer and electronic modules and adapted for on-site, multiple, drop test measurements to obtain in real-time and/or for historical records the characteristics or suitability of surfaces for their intended use.

This surface resiliency tester is adaptable to a variety of configurations depending on the surface to be tested and the characteristics to be obtained.

BACKGROUND OF THE INVENTION

Each year many thousands of children and adults are injured in playgrounds, and public and private reaction and sports facilities as a result of falls on inadequately prepared surfaces. Lawsuits of several million dollars are common where playground accidents have occurred. Insurance companies are now becoming much more selective in granting coverage and in many instances are denying institutions liability protection. Studies reported by the Consumers Product Safety Commission, for instance, have estimated that a head injury tolerance limit for head-first falls of children are 150–200 g's average acceleration for 3 milliseconds or 200–250 g's peak acceleration. Surfaces composed of synthetic materials currently exist that will adequately protect against these levels, but such materials are costly and only a few institutions and businesses can afford the installation expense. For the several hundred thousand public playgrounds in school districts and recreation departments throughout the country, such materials and installations are too costly. Public authorities must rely on less expensive installations, such as sand beds, pea gravel, shredded tires, and mulch. However, no uniform guidelines exist as to amounts and thicknesses of these materials that are required to produce safe g levels in the event of a fall. Furthermore, no apparatus or method is currently available which can be handcarried to a site, used on a frequent basis by individuals unskilled in conducting tests or obtaining test measurements.

The invention herein describes an apparatus and method which will provide these functions. It is simple to operate, measures impact g levels in real time, can be used for hundreds of impact tests without loss of accuracy, is hand portable, and inexpensive. It can be seen from following U.S. patent briefs, that prior art cannot provide the functions provided by the current apparatus and method.

In Kirkland U.S. Pat. No. 4,492,111, the invention relates to a projectable penetrometer which provides mechanisms for measuring rheological and other properties as well as electrical resistance and resistivity of materials, and/or acoustic monitoring of various types of remote or otherwise inaccessible surfaces including land areas, sea and river bottoms. The apparatus employs a multitude of sensing elements and is further characterized by the presence of at least three electrode pairs. As onboard power supply is included together with telemetry equipment to generate ground characteristics and transmit such signals. In use, the device is dropped or thrust from the host vehicle such as a ship, aircraft or spacecraft and allowed to penetrate the inaccessible surface. It is then dragged along a pre-described track as measurements are telemetered to the host vehicle. Re-tracking provides comparative information from that received by the initial track.

This apparatus is expensive to manufacture and operate, cannot be easily transported to a test site and requires highly skilled individuals to operate and interpret the data.

Baker's invention U.S. Pat. No. 4,245,510 relates to a portable accelerometer device mounted by suspension means in a housing and adapted for use to measure accurately the magnitude of a load applied to a vehicle, ship, floating bouy or some other transportation device. The device measures excursions from a datum due to an applied load on a vehicle and will overcome many of the problems associated with the use of stabilized platform assemblies for measuring vertical loads applied to towed bodies and/or the towing cable with its associated couplings. Applied vertical loads are measured by a mechanical pendulum assembly mounted by suspension in a housing and having an accelerometer as its load sensing device. An output signal is generated in response to displacements due to applied loads. This apparatus cannot be adapted for on-site drop tests and required skilled operators to conduct tests and analyze data obtained by the apparatus.

In Wilson et al U.S. Pat. No. 3,788,466 the device is one that is used in a material sorting system. An accelerometer is mounted on a movable, rigid, pendulum-like arm adapted to strike individual pieces of material moving along a conveyor system. The accelerometer measures the rate of deceleration of the pendulum-like arm as it strikes material producing a signal waveform. This signal is then fed to an electronic coding apparatus which compares this received waveform to typical waveforms stored in computer memory. When a match is made, the material is routed to its proper receptacle. The object of this invention is to provide a coding and switching system for use in automated, solid-refuse sorting.

Specker et al U.S. Pat. No. 4,161,874 relates to a head and neck impact measuring system consisting of a movable plate member with an anthropometric (dummy) head and neck secured to the plate. Force measuring cells are mounted in the horizontal and vertical planes of the supports and the dummy head and triaxial accelerometers at the CG of the dummy head. The device is for measuring head accelerations and impact forces to determine moments reacted through the base of the neck. The invention is primarily aimed at evaluation of injury potential to pilots and aircraft crew members in bird-aircraft midair collisions. These collisions often result in an impact of the aircraft canopy with the pilot's helmet.

In Yamawaki et al U.S. Pat. No. 4,11,039, a bench or laboratory apparatus for measuring the hardness of rubber is patented. This device provides an improved mechanism for measuring the hardness of rubber with a high degree of reliability and accuracy. The device provides a means of pressing a needle-like probe against the surface of a sample at a predetermined velocity and force and for maintaining the reaction of the sample acting on the needles at a constant value thereby increasing measurement accuracy. The measurement is detected by a transducer and processed by an electronic circuit eliminating errors induced by moving pointers and operator skill.

Fletcher's invention in U.S. Pat. No. 3,972,038 relates to an accelerometer telemetry system incorporated in a finger ring and is used for monitoring motor responses of a subject. The system includes an accelerometer, battery and transmitter and provides information to a remote receiver regarding hand movements of a subject wearing the ring. The system includes a miniaturized semiconductor strain gauge coupled to a seismic mass for detecting movements and for producing an electrical output signal. The output signal is used to modulate an RF transmitter. The entire sensing and transmitting package including the power sources is contained in a case or housing the size and shape of a finger ring.

Yakshin et al U.S. Pat. No. 4,030,339, relates to a device for automatic selection of the range of peak acceleration measurements. The object of the invention is to provide electronic circuitry which would make it possible to automatically select a required measurement range and thus increase the operating speed of impact impulse measurements. Automatic range selection is achieved through a series of amplifiers, comparators and D/A conversion circuitry.

Brands U.S. Pat. No. 3,888,108 relates to an apparatus for detecting transmission of an energy impulse through pavement as an indicator of its structural condition. Impact is provided by a hammer that falls vertically when manually released. A pair of spaced transducers operating as accelerometers in contact with the pavement produce electrical signals related to the magnitude of the energy impulse transmitted through the pavement to them. These signals are monitored, rectified, integrated, and used with readout circuitry to calculate a useful numerical value indicative of pavement structural conditions. In use, the device is hand-carried to a test site and the pavement excited with a shock wave or impulse provided by the falling hammer. The vibrational response is subjected to a complex wideband analysis to extract useful information concerning pavement strength. Skilled engineers are required to conduct the tests and to conduct the analyses necessary to determine structural conditions.

In Messner U.S. Pat. No. 3,365,929, the invention relates to a portable, impact shock testing device to provide for dynamically testing shock transducers in the field where conventional devices are either unavailable or their use was impractical. The tester is used principally for checking the output of the piezoelectric accelerometers immediately prior to field use. The output of the accelerometers undergoing test is connected to an oscilloscope for indicting the shock pulse. This is a device for testing transducers such as piezoelectric accelerometers and as such is not useful for on-site drop testing to obtain surface characteristics.

In Costello et al U.S. Pat. No. 3,298,222, the invention is an apparatus for measuring remote and relatively inaccessible surface characteristics to determine its load bearing properties. The device is comprised of a hydrodynamically designed vehicle which is dropped from a ship and allowed to gravitationally impact the surface beneath a body of water. An accelerometer or transducer on the device is connected by a cable to shipboard monitoring equipment. The signal thus produced is an indication of the load bearing characteristics of the bottom surface.

Falkner's invention of U.S. Pat. No. 3,149,606 relates to a simple shock device which gives an indication of when it has been subjected to a shock force of more than a given value. Such a device is particularly useful for showing whether cargo has been subjected to excessive shock during transit or handling. It consists of at least two weights which are spring loaded against supports so that a non-axial acceleration of more than a given value will displace a respective weight from its support and the consequent position of the weight will show that a pre-determined acceleration has been exceeded.

While the foregoing references describe various means of obtaining test measurements with impact devices, none are hand-portable or capable of obtaining multiple, on-site, drop test measurements of natural or synthetic surfaces nor are they capable of being dropped from various heights to simulate head-first falls by children.

SUMMARY OF THE INVENTION

According to the present invention, a hand-portable surface resiliency tester apparatus is provided which when dropped from appropriate heights will register an instantaneous indication of the peak impact g level which is then related to the type and characteristics of the impacted surface. The apparatus includes a transducer module and an electronic module which may be a single, self-contained apparatus or two separate modules with interconnecting cabling. The entire apparatus including a power source is contained in a package the size, shape and weight of an elongated bowling ball with a hand grip, thus permitting the apparatus to be easily hand-carried to a test site and dropped many times from various heights and locations within the test site to obtain real-time and recorded measurements of surface characteristics. The transducer module includes a transducer fixed to an impact head mass along the vertical centerline and on or slight above the c.g. which will produce an electrical output signal at the moment of impact proportional to the peak impact g level. The signal is detected at its peak and operated on to convert the signal to a g level indication. The invention provides for the easy replacement of the impact head and may be constructed of any suitable material such as steel, aluminum or plastic and, depending on the application, may be formed in a variety of configurations. The invention is constructed so as to produce a center-of gravity along the vertical centerline $A_v$ within the impact head. The center of gravity $C_g$ is preferably located at the interface of the transducer locating surfaces (see $C_g$ in FIG. 3) providing a directionally stable configuration assuring that the impact forces will always act along the vertical centerline regardless of the drop height and thus obtain reliable and true measurements. This arrangement minimizes the possible harmful effects of an off-center impact.

The electronics module may be constructed of any suitable material such as plastic or aluminum. It contains circuits to receive, condition, convert, store and display values correlated to the transducer output signal level and when assembled to the transducer module completely encloses, supports, and protects the electronics therein. Power to operate the apparatus may be housed in the electronics module or externally.

The invention is intended to be used on a frequent basis by a single individual, unskilled in the field of conducting and obtaining on-site test measurements. Repeated drop tests from appropriate heights and site locations with immediate indication of the impacted surface characteristics are obtainable with a minimum of instruction. Playground supervisors, for instance, may be required to maintain play surfaces within certain standards by conducting drop tests, recording the measurement and to take remedial action is so indicated.

One object of this invention is to provide a self-contained, hand-carriable apparatus which will conveniently and easily permit the acquisition of multiple, on site, reliable, drop test measurements of various surfaces.

Another objective is to provide a convenient manual apparatus for surface resiliency testing which will aid in the design of playground, sports, and other surfaces.

Another objective of this invention is to provide an apparatus and method that is simple in operation and provides instantaneous readings.

Yet another objective is to provide a device that can be used reliably at frequent intervals to maintain surface resiliency conditions within pre-determined standards.

Still another objective of this invention is to provide a device that can be used to establish surface resiliency standards for various applications.

A further objective of this invention which is a corollary to the foregoing objectives is to provide a hand-carriable device that can be adapted to a variety of impact heads and will conveniently and easily permit the acquisition of surface compactness/hardness, drop test measurements.

Another objective is to provide a device that can be adapted to a variety of impact heads that will conveniently and easily permit the acquisition of surface penetration measurements.

Another objective is to provide a device that can be adapted to a variety of transducer types that will conveniently and easily permit the conversion of impact forces to proportional electrical signals.

These and further objectives will be obvious from the following disclosure, taken together with the accompanying drawings. The drawings and detailed description illustrate a preferred embodiment of this apparatus.

BRIEF DESCRIPTION OF THE DRAWINGS

These and other object of the present invention and the various features and details of the operation and construction thereof are hereinafter more fully set forth with reference to the accompanying drawings, wherein.

DETAILED DESCRIPTION OF THE PREFERRED EMBODIMENT

Although the present invention can be adapted for many varied uses, the following detail description will serve to illustrate one embodiment.

Figure 1:
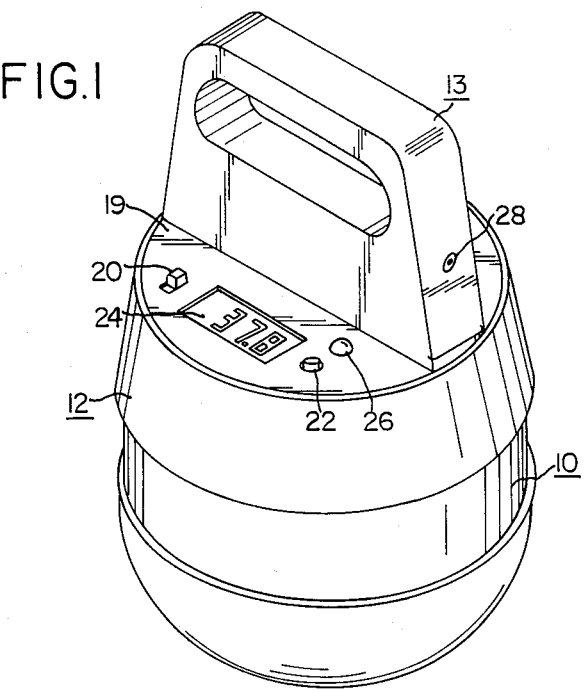
FIG. 1 is a perspective view of the surface resiliency tester (SRT) showing the two major sub-assemblies, the transducer module and the electronic module and illustrates one form of the SRT described herein with a hemispherical transducer module.

The general SRT configuration shown in FIG. 1 is modularly constructed and consists of a transducer module 10 and in this embodiment integrated and fixably attached to an electronic module 12 to form a single self-contained hand-portable SRT, adapted for drop testing the resiliency or hardness of playground, recreational or other type surfaces or soil where the condition of the surface or soil may be the most influential factor in the degree of trauma caused by an accidental fall. A central handle 13, for carrying and manual operation purposes and containing a compartment 16 for housing a 9 volt DC, rechargeable battery forms part of the electronic module 12. The upper outer surface 19 of the electronic module 12 contains suitable openings to accommodate, for example, a main on/off switch 20, a reset button 22, a readout device in the form of an LCD or LED 24, a low-battery voltage indictor 26, and the like. A battery charging jack 28 in the central handle 13 may be provided to connect a battery charger to the rechargeable battery.

Figure 1B:
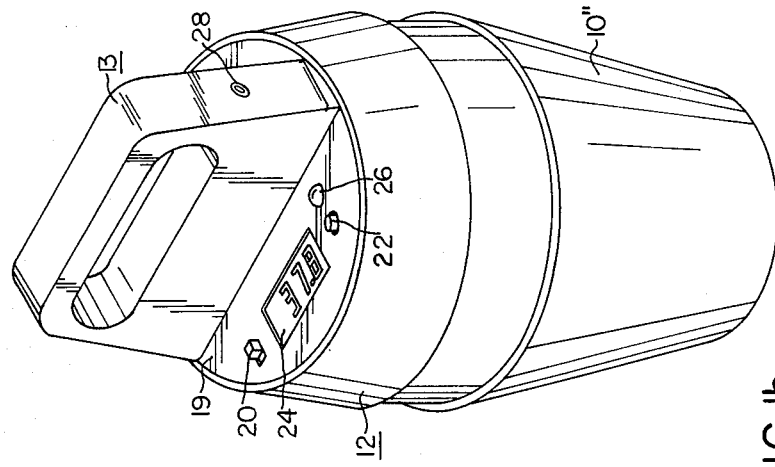
FIGS. 1a and 1b illustrate the adaptation of several impact head shapes for the transducer module for testing and measuring soil compactness and natural or synthetic surface hardnesses.
Figure 1A:
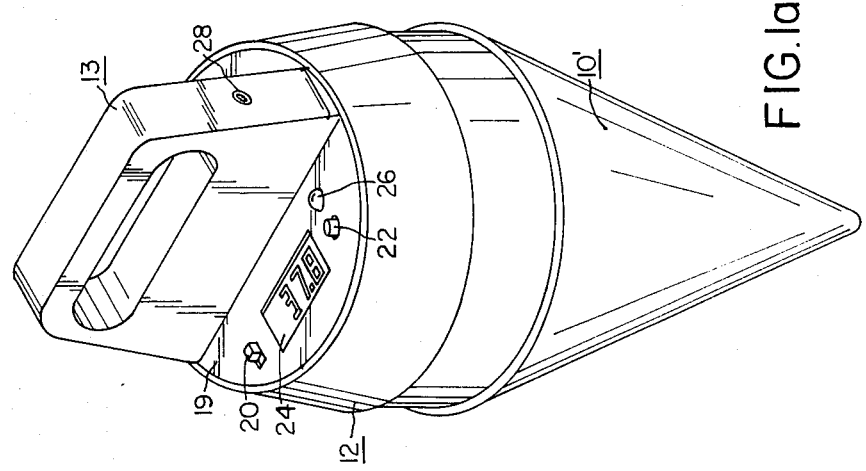
Figure 4:
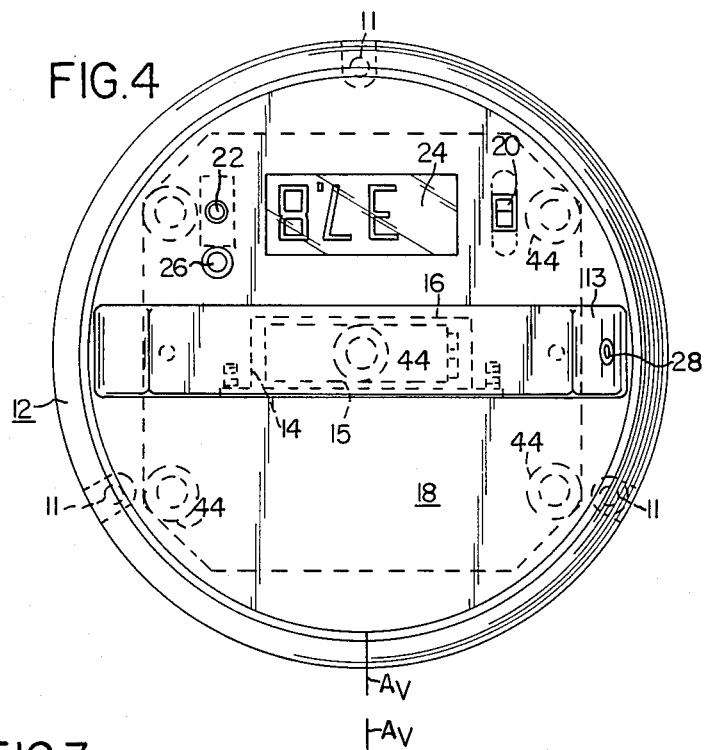
FIGS. 3 and 4 are elevation and top views respectively of the SRT with cutaways to show pertinent construction and assembly details.

The transducer module 10 can be constructed in a variety of impact head configurations as shown in FIGS. 1a and 1b adapted for use, for instance, to measure soil suitability for load bearing structures or suitability of certain materials to absorb impact forces.

Figure 2:
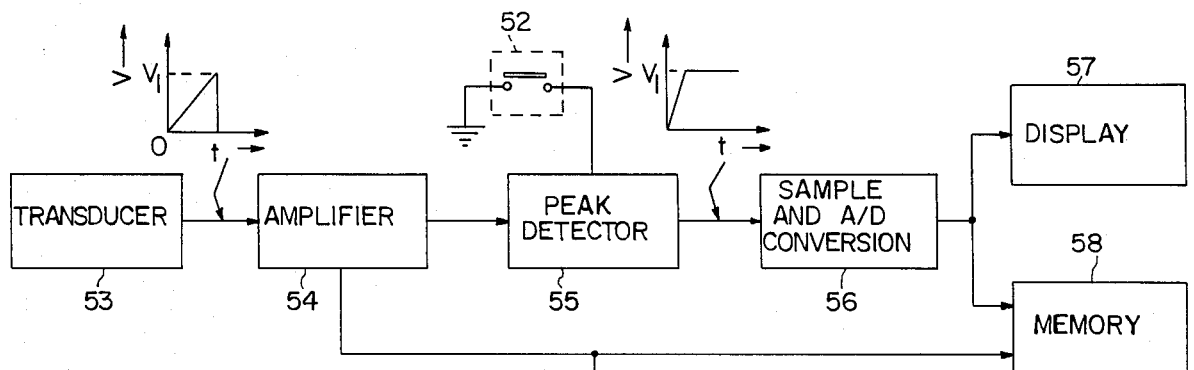
FIG. 2 is a block diagram of the sensing, detection, conversion, display, memory, microprocessor and printer functions.

Referring now to FIG. 2, showing a diagram of one example of the surface resiliency tester, the impact measurement is started by closing switch 50 applying power from battery 51 to all active elements in the electronics, and depressing reset switch 52 to discharge the peak detector preparing it for the next test. The apparatus is then manually raised to the height from which a fall is being simulated and allowed to free-fall to the surface. During free-fall the transducer 53 output is zero and is calibrated to produce a signal proportional to the impact g level. At the moment of impact, a voltage signal is generated and continues to increase, illustrated, as $V_1$, in FIG. 2 until the apparatus has decelerated to zero velocity at which time the voltage signal falls rapidly back to zero as shown. The signal thus generated may be amplified by 54 and then applied to a peak detector 55. The peak detector 55 is constructed to detect and hold the maximum voltage value $V_1$ which is proportional to the peak impact g level. The analog-digital converter 56 operates to convert the electrical signal voltage $V_1$ in a numerical equivalent of the voltage $V_1$ and displaying the impact g's by digits on display 57 and/or for storing in a memory device 58 or operating other devices, for example, a microprocessor 59 and printer 60. Upon completion of a drop test, the reset button 52 is depressed for resetting the peak detector preparing it for the next measurement.

As described above, all active electronic elements are powered by a battery 51. The invention also provides for re-charging the battery 61 and for determining the charge state of the battery through the "low voltage" indicator 62 and switch 63.

Figure 3:
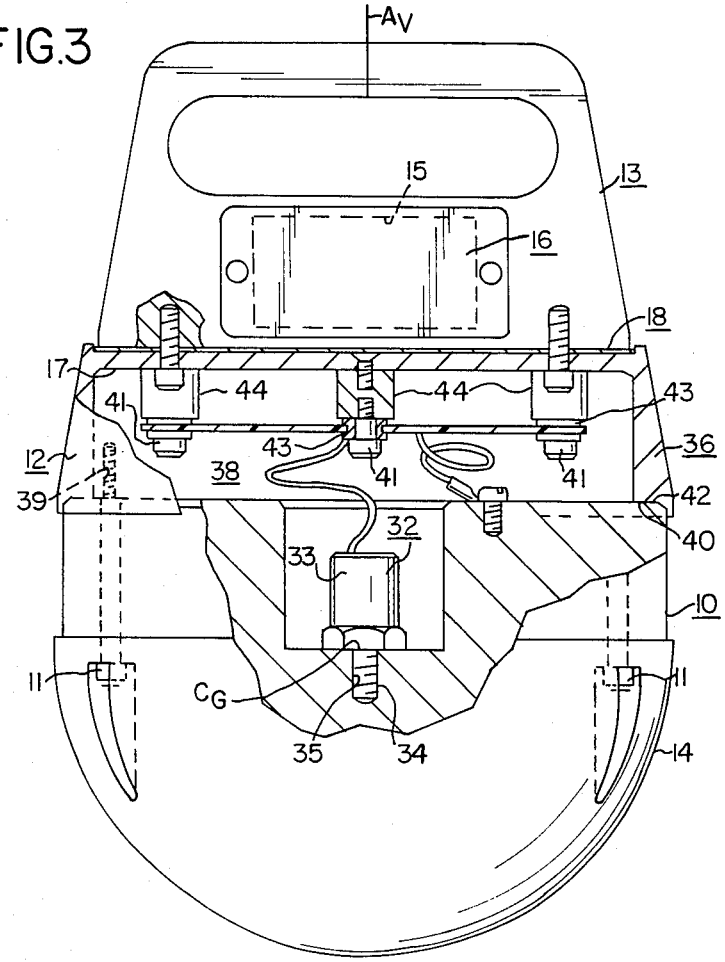

Referring to FIG. 3, the transducer module 10, which consists of the impact head 14 and the transducer 32, is hemispherically shaped, approximately 6" in diameter and, in this embodiment, constructed entirely of aluminum, Three equally spaced, recessed bolts 11 on a 5¼ inch diameter bolt circle provide for fixably attaching the electronics module 12 to the transducer module 10. A circular shoulder 42 at the base of the electronic module 12 confronting and mating to surface 40 on the upper face of the transducer module 10 provides for the installation of a shock absorbing system which may consist of springs and/or shock absorbing material. In this embodiment, the two surfaces 40 and 42 are in direct contact without any intervening shock absorbing mechanism or material.

The transducer module 10 is also adapted for accepting a variety of transducers for measuring a wide range of impact forces and durations. In the present embodiment, the transducer 32 is an accelerometer fixably and rigidly attached to the impact head 14 by a threaded stud 34 integral to the accelerometer housing 33 engaging a threaded hole 35 in the impact head 14. The integral body thus formed eliminates attenuation to the accelerometer 32 of the impact force sustained at the impact head 14. Other transducer attachment methods may be used to achieve the same end.

Except for the mounting surfaces between the impact head 14 and the accelerometer 32 the entire surface of the impact head 14 is anodized for protection against potentially corrosive elements and to provide a non-conducting barrier to minimize static electricity build-up.

Although the transducer in the present embodiment is an accelerometer, other types of transducers, for instance, force balance types, strain gauges or load cells and the like may be used as force sensing elements. The accelerometer 32 in the present embodiment is a single-ended, piezoelectric, compression type accelerometer which produces an electrical output signal directly proportional to the impact force level when an acceleration or deceleration is applied to the SRT level without the necessity of an external power source or carrier voltage.

Referring again to FIG. 3, the electronic module 12, in the present embodiment, consists of the housing 36, an electronics board 38, a central handle 13, and a 9 V DC battery 15. The lower portion of the housing 36 includes threaded holes 39 for securing the electronics module 12 to the transducer module 10. A shoulder 42 at the interface of the two modules rests on and is supported by a confronting mating shoulder 40 on the transducer module 10. When bolted together clearance bolt holes in the transducer module match up with the threaded holes 30 on the electronic modules 12 allowing relative motion between the two modules. An annular shock absorbing material (not shown) between the two confronting shoulders and acts to absorb some of the shock transmitted to the electronics module at impact.

The upper, internal surface 17 of electronics housing 36 contains support posts 44 for securing the electronic board to the upper surface 17 of housing 36, and in the present embodiment, the electronics are mounted on a printed circuit board (PCB) 38 and protected against shock damages by securing the PCB 38 to the upper surfaces 17 of housing 36 with 5 threaded attachments 41 engaging the support posts 44. Rubber or shock absorbing washers or grommets 43 placed between the PCB 38 and the support posts 44 provide shock isolation to the electronics. The outer upper surface of housing 36 contains a control and display panel 18 and a central hand grip 13. The control and display panel 18 provides locations for and easy access to the on/off switch 20, reset switch 22, low battery voltage indictor 26, and a liquid crystal display 24.

Figure 5:
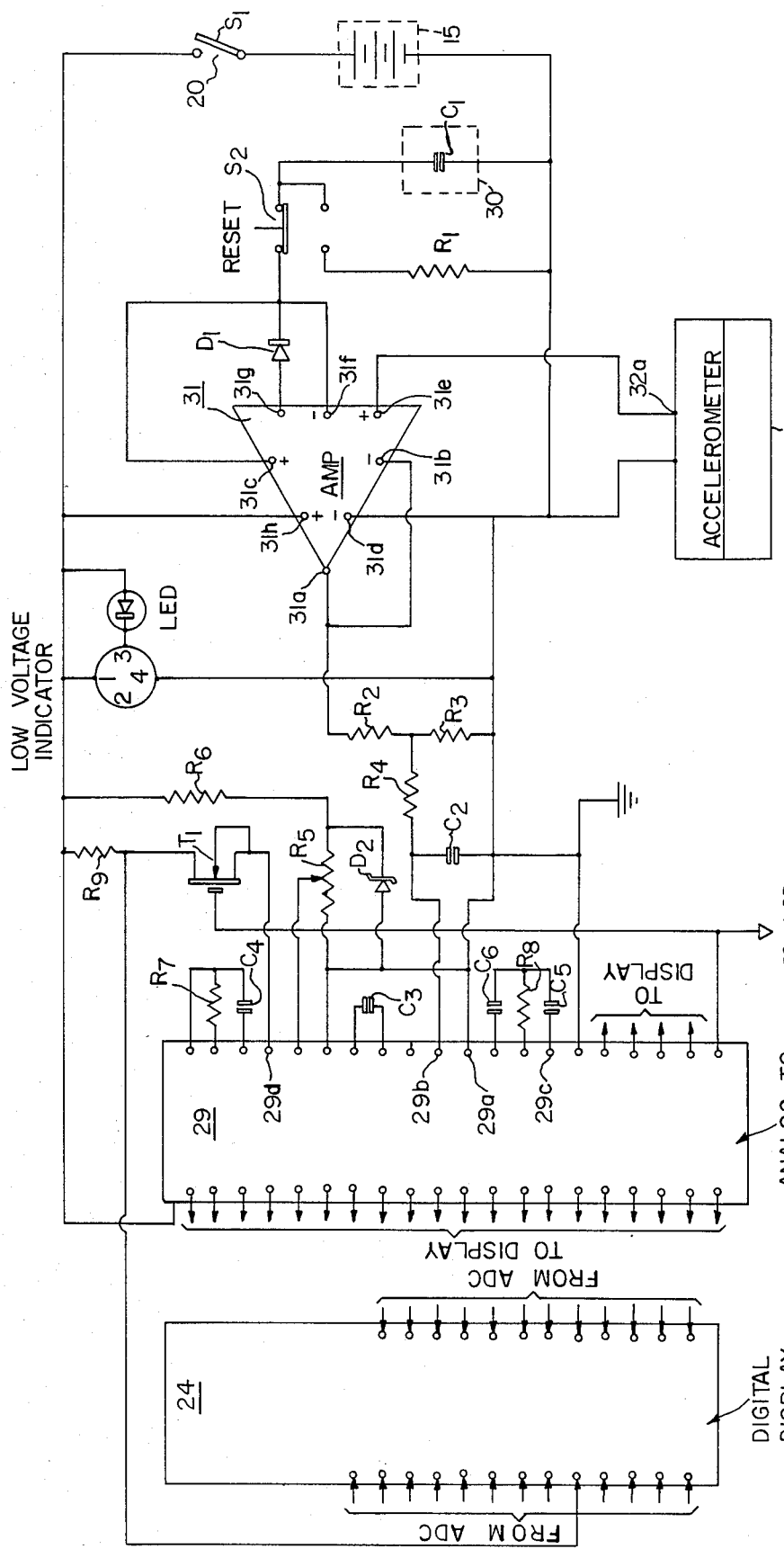
FIG. 5 is a detailed circuit diagram illustrating one form of the electronics described in the preferred embodiment.

Turning now to FIG. 5, the electrical circuitry of the present embodiment is illustrated as containing a 9 V DC battery 15, a piezoelectric accelerometer 32, an operational amplifier 31, a peak detector 30, an A/D converter 29 with appropriate ancilliary components, and a digital display 24. The electrical circuitry excluding the accelerometer are energized by the 9 V DC battery 15 through switch 20.

Although the following are detailed descriptions and operation of the major elements of the hand-portable surface resiliency tester cited above, it is to be understood that the electronics could take a variety of different forms to achieve the same functional results.

Deceleration forces at the moment of impact are registered by accelerometer 32 which is a single ended piezoelectric, compression type transducer used in a common mode application and designed to deliver 6 V DC at full scale impact g's. One such commercially available accelerometer is known as Columbia Research Labs Model 3000 series which will deliver 30 mv/g nominal and can output a linear response for input signals in excess of 7 KHz. As described earlier, when the apparatus is dropped accelerometer 32 outputs a voltage signal across 31$d$ and 31$e$ which is proportional to the deceleration force. This signal is fed to the dual operational amplifier 31 used as a voltage follower and current amplifier. The op. amp. is essentially a unity gain amplifier with very low resistance at the input 31$e$ from the accelerometer output 32$a$ to the op. amp. 31. The output 31$g$ of the voltage follower amplifier is fed to the input 31$c$ of the current amplifier through diode $D_1$ and back through the inverting input 31$f$. The effect of this arrangement is to allow rectification and peak detection of signals whose peak voltages are in the millivolt region, i.e. much less than the diode $D_1$ offset voltage. Furthermore, when diode $D_1$ is on, the negative feedback through 31$f$ produces an output impedance approaching zero. For this reason, the charging time constant through capacitor $C_1$ shrinks to a very small value, eliminating source effects. The net effect of this circuit arrangement is to allow a full range of impact g values (from below 5 g's up to 1999 g's) to be obtained by the apparatus.

The output 31$a$ from op. amp. 31 as depicted by $V_1$ in FIG. 2 is fed to the analog-to-digital converter 29 through a voltage divider network $R_2$, $R_3$, and $R_4$ to reduce the voltage input at 29$a$ and 29$b$ to a level compatible with A/D converter 29 circuitry. One such commercially available converter is known as Intersil ICL 7106 ADC. In addition, the conversion functions described in the following paragraphs need to be adjusted for compatibility with the specific use of this apparatus.

Reference voltage: Since the input common 29$a$ is tied to ground, an external reference voltage is required to generate full scale output. The reference voltage is established by reference capacitor $C_3$ and zener diode $D_2$ with $R_5$ acting as a variable vernier resistance for fine tuning the reference.

Integrating Capacitor: The A/D converter 29 internally integrates the input signal across 29$a$ and 29$b$. Capacitor $C_5$ at 29$c$ is selected to allow maximum voltage swing of the input without saturating the integrator swing.

Sampling frequency: Capacitor $C_4$ and resistor $R_7$ are selected to produce a sampling frequency consistent with the voltage decay of the output voltage 31a of op. amp. 31 stored in capacitor $C_1$.

Overload and noise: Capacitor $C_6$ is selected to increase the recovery speed from overload and to reduce system noise. The electrical components described herein are commercially available. The following table will identify those elements illustrated in FIG. 5:

| | | |
|---|---|---|
| $R_1$ = 470 ohms | $R_7$ = 100K ohms | $C_4$ = 100 pf |
| $R_2$ = 1M ohms | $R_8$ = 470K ohms | $C_5$ = 0.22 $\mu f$ |
| $R_3$ = 470K ohms | $R_9$ = 1M ohms | $C_6$ = 0.047 $\mu f$ |
| $R_4$ = 1M ohms | $C_1$ = 100 $\mu f$ | $D_1$ = 1N4001 |
| $R_5$ = 20K ohms | $C_2$ = 0.01 $\mu f$ | $D_2$ = 1CL8069 |
| $R_6$ = 6.8K ohms | $C_3$ = 0.1 $\mu f$ | |

Fixed decimal point: an inverter transistor $T_1$ at 29d is used for generating a negative external supply to drive a fixed decimal point. In the current embodiment, an Intersil transistor IT 1750 is used to locate a fixed decimal point between the third and last digits. (May be eliminated if desired).

The output of the A/D converter 29 are discrete voltages applied to appropriate segments of each digit in the display 24 corresponding to the digital representation of the voltage generated by accelerometer 32. The display in the current embodiment is an Amperex 3½ digit liquid crystal display and is capable of representing g levels up to 1999.

The foregoing description relates to a particularly useful hand-portable surface resiliency tester. Modifications and changes will be apparent to those knowledgeable in this art, as may be indicated by varied uses. The invention has useful application in testing a variety of surfaces in the sports and construction fields. It is intended within the scope of this invention to encompass all such changes and modifications as fall within the scope of the claims below.

What is claimed is:

1. A hand-portable, self contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's and said electronic module including means for converting said electrical signals from the transducer means to indicia means of said electrical signals relatable to the characteristics of the surface under test and a shock isolation-/absorbing system at the interface between the transducer and electronic modules.

2. A hand-portable, self contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's and said electronic module including an electronic circuit board and means for converting said electrical signals from the transducer means to indicia means of said electrical signals relatable to the characteristics of the surface under test and a shock absorbing system supporting the electronic circuit board.

3. A hand-portable, self contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's and said electronic module including means for converting said electrical signals from the transducer means to indicia means of said electrical signals relatable to the characteristics of the surface under test and means permitting re-charging of the tester via a DC battery power source.

4. A hand-portable, self contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's and said electronic module including means for converting said electrical signals from the transducer means to indicia means of said electrical signals relatable to the characteristics of the surface under test and means for detecting, converting, and displaying electrical signals or alpha numeric representations of multiple alpha numeric representations and/or recording drop tests in real-time.

5. A hand-portable, self contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's, said electronic module including means for converting said electrical signals from the transducer means to indicia means of said electrical signals relatable to the characteristics of the surface under test whereby said impact forces or g's are displayed upon display means located on said electronic module.

6. A surface resiliency tester according to claim 5, wherein the apparatus is hand carriable to facilitate multiple, on-site drop test measurements.

7. A surface resiliency tester according to claim 5, wherein the transducer and electronic modules may be integrated into a single, self-contained apparatus.

8. A surface resiliency tester according to claim 5, wherein the transducer and electronic modules may be separate, hand-held components connected by appropriate cabling.

9. A surface resiliency tester according to claim 5, wherein the transducer and electronic modules may be separate, hand-held components connected by transmitted RF signals.

10. A surface resiliency tester according to claim 5, wherein the transducer module is adapted to accept a variety of impact heads individually configured to test and measure natural and synthetic surfaces for resiliency, compactness or hardness characteristics.

11. A surface resiliency tester according to claim 5, wherein the transducer module is adapted to accept a variety of transducer means; e.g. piezoelectric accelerometers, force balance accelerometers, load cells, strain gages and the like for converting drop impact forces or g's to proportional electrical signals.

12. A surface resiliency tester according to claim 5, wherein the apparatus is adapted to accept and operate from either an AC or DC power source.

13. A surface resiliency tester according to claim 5, wherein the apparatus is adopted to detect, convert, and store impact drop test electrical signals and/or alpha numeric representations of electrical signals for non real-time use, analysis, recording and/or display.

14. A hand portable tester as claimed in claim 5, wherein the transducer is located on the line through the central axis of the head adjacent the center of gravity.

15. A hand portable, self-contained surface resiliency tester having a transducer module and an electronic module adapted to obtain multiple drop test measurements of the in-site resiliency, compactness and hardness characteristics of natural and synthetic surfaces, said transducer module comprising an impact head and a transducer means suitable for producing an electrical signal proportional to impact forces or g's, said electronic module including means for converting said electrical signals relatable to the characteristics of the surface under test, the center of gravity being located at the interface between the transducer and electronic modules thereby providing a directionally stable configuration ensuring that the impact forces or g's will act along the central axis through the transducer and electronic modules to minimize the effects of an off-center impact.

16. A hand portable tester as claimed in claim 15, wherein the impact head is hemispherically shaped.

17. A hand portable tester as claimed in claim 15, wherein the impact head is coneshaped.

18. A hand portable tester as claimed in claim 15, wherein the impact head is in the shape of a truncated cone.

* * * * *